United States Patent [19]
Sakai et al.

[11] Patent Number: 5,376,104
[45] Date of Patent: Dec. 27, 1994

[54] DEFIBRILLATOR WITH ELECTROCARDIOGRAM MONITOR

[75] Inventors: Yoshio Sakai; Ikuhiro Tsumura; Nobutaka Kobayashi, all of Tokyo, Japan

[73] Assignee: Nihon Kohden Corporation, Tokyo, Japan

[21] Appl. No.: 12,228

[22] Filed: Feb. 2, 1993

[30] Foreign Application Priority Data

Feb. 7, 1992 [JP] Japan .................. 4-012861[U]

[51] Int. Cl.$^5$ .............................................. A61N 1/39
[52] U.S. Cl. ........................................ 607/5; 128/696; 128/908
[58] Field of Search ............. 607/5, 63; 128/695, 128/696, 908

[56] References Cited

U.S. PATENT DOCUMENTS

| | | | |
|---|---|---|---|
| 3,569,852 | 3/1971 | Berkovits | 128/696 |
| 3,580,243 | 5/1971 | Johnson | 128/696 |
| 4,235,242 | 11/1980 | Howson et al. | 128/695 |
| 4,261,369 | 4/1981 | Allor | 128/696 |
| 4,446,172 | 4/1984 | Langer | 128/908 |
| 4,453,547 | 6/1984 | Castel et al. | 607/63 |
| 4,494,552 | 1/1985 | Heath | 128/696 |
| 4,934,377 | 6/1990 | Bova et al. | 128/696 |

FOREIGN PATENT DOCUMENTS

| | | | |
|---|---|---|---|
| 0072144 | 2/1983 | European Pat. Off. | |
| 0353341 | 2/1990 | European Pat. Off. | 607/5 |

Primary Examiner—William E. Kamm
Attorney, Agent, or Firm—Hoffmann & Baron

[57] ABSTRACT

In a defibrillator with an electrocardiographic monitor which monitors electrocardiographic signals induced at electrodes by means of a preamplifier and supplying the signals to an electrocardiographic signal processing circuit through high-pass filters, the dynamic range of a preamplifier is made wider in accordance with the amplitude of a polarization voltage which is developed when a defibrillator is operated. A high-pass filter is formed of a first high-pass filter which operates in a normal state and a second high-pass filter whose blocking frequency is higher than that of the first high-pass filter so that the polarization voltage is attenuated without erasing the electrocardiographic signals. The second high-pass filter is operated in synchronization with the operation of the defibrillator during a time period corresponding to the time period in which the polarization voltage is generated.

4 Claims, 6 Drawing Sheets

10 SECONDS

DEFIBRILLATOR WITH ELECTROCARDIOGRAM MONITOR

BACKGROUND OF THE INVENTION

1. Field of the Invention

The present invention relates to a defibrillator with an electrocardiographic monitor which displays and records electrocardiographic signals, or performs data processing by amplifying electrocardiographic signals induced at electrodes by means of a preamplifier and then supplying the signals to an electrocardiographic signal processing circuit through high-pass filters.

In such a defibrillator with an electrocardiogram monitor, when the defibrillator is operated, a polarization voltage greater than an ordinary signal level is generated between electrodes as a result of the application of a high voltage. Therefore, an electrocardiograph is provided with an instantaneous switch for grounding an output end of a coupling capacitor which forms a high-pass filter when a high level signal, as well as such polarization voltage, is instantaneously input at the time of electrode switching or the like. This instantaneous switch prevents the scale-over of an abnormally high level signal in an output unit.

However, there are some cases in which the amplitude of the above-mentioned polarization voltage at high voltage application time reaches approximately ±300 mV and then gradually decreases in 10 seconds or thereabouts. If the instantaneous switch is operated to prevent the scale-over or the like, electrocardiographic signals are completely vanished.

SUMMARY OF THE INVENTION

Accordingly, an object of the present invention is to provide a defibrillator with an electrocardiographic monitor capable of detecting electrocardiographic signals at near a base-line level immediately after the defibrillator is operated.

To this end, according to the present invention, the dynamic range of a preamplifier is made wider in accordance with the amplitude of a polarization voltage which is generated when a defibrillator is operated. A high-pass filter is formed of a first high-pass filter which operates in a normal state and a second high-pass filter whose cut-off frequency is higher than that of the first high-pass filter so that the polarization voltage is attenuated without vanishing the electrocardiographic signals. Filter switching means is provided for operating the second high-pass filter in synchronization with the operation of the defibrillator during the time period corresponding to the time period in which the polarization voltage is generated.

According to the present invention, since the cut-off frequency of the high-pass filter becomes temporarily higher when the defibrillator is operated, it is possible to suppress an input of a polarization voltage and very quickly control the vanishing time of the electrocardiographic signals.

If two types of high-pass filters are formed of digital filters, it is possible to switch filter characteristics at high speed and suppress transient signal changes.

The above and further objects and novel features of the invention will more fully appear from the following detailed description when the same is read in connection with the accompanying drawings. It is to be expressly understood, however, that the drawings are for the purpose of illustration only and are not intended as a definition of the limits of the invention.

DETAILED DESCRIPTION OF THE PREFERRED EMBODIMENTS

Figure 1:
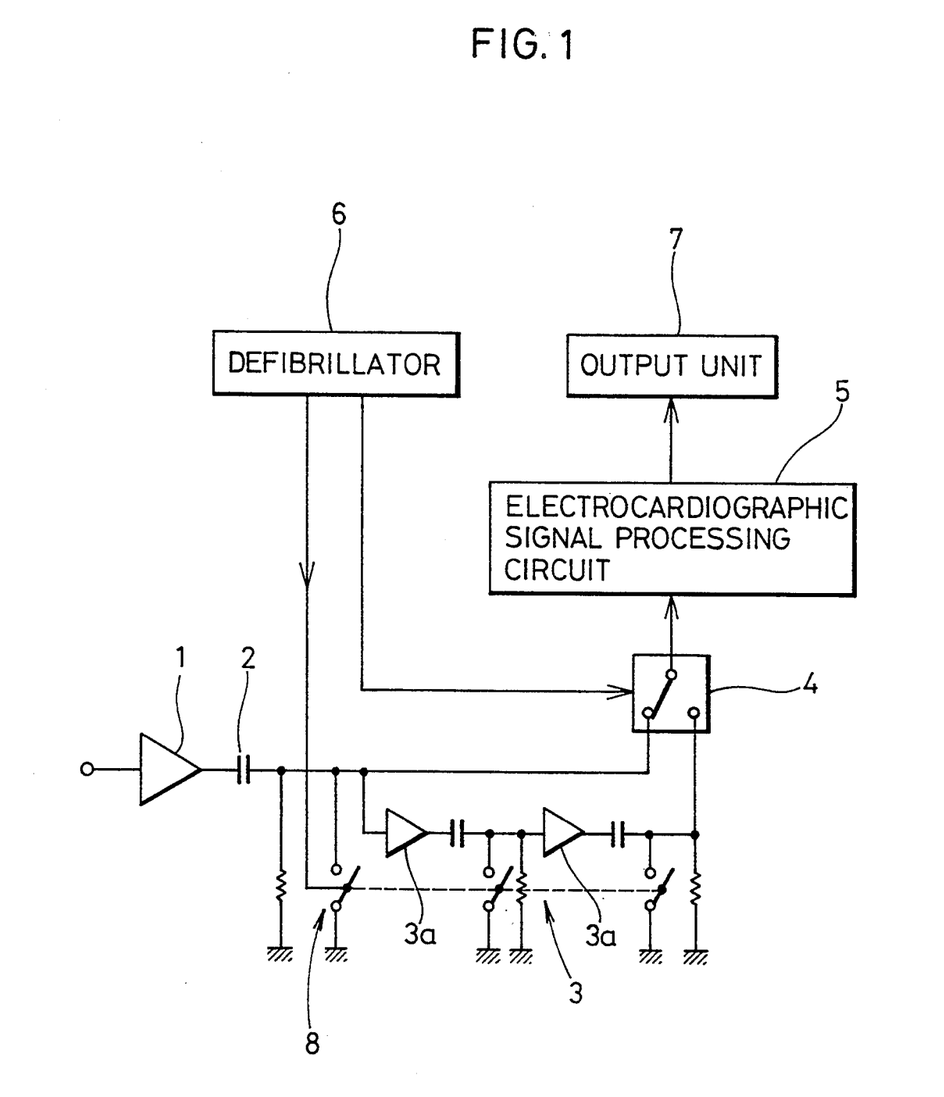
FIG. 1 is a view illustrating the circuitry of the main portion of a defibrillator with an electrocardiographic monitor according to an embodiment of the present invention.

FIG. 1 illustrates a defibrillator with an electrocardiographic monitor according to an embodiment of the present invention. Reference numeral 1 denotes a preamplifier for amplifying electrocardiographic signals induced at electrodes, which preamplifier has a dynamic range of ±500 mV in proportion to a polarization voltage of approximately ±300 mV which develops as a result of the application of a high voltage when a defibrillator 6 is operated. Reference numeral 2 denotes a high-pass filter having a time constant of 0.52 seconds, i.e., the cut-off frequency is approximately 0.3 Hz. Reference numeral 3 denotes a high-pass filter having a third-order cut-off frequency of approximately 0.6 Hz in which RC circuits of the same time constant are cascade-connected in two steps to the high-pass filter 2 through a preamplifier 3a. Reference numeral 4 denotes a filter switching circuit which operates the high-pass filter 3 for, for example, 10 seconds, which is the time period the polarization voltage is generated, in synchronization with a trigger signal which operates the defibrillator 6. Reference numeral 5 denotes an electrocardiographic signal processing circuit for amplifying or converting the electrocardiographic signals transmitted in an analog form through such high-pass filter to a digital form and for performing data processing, the result of the processing being displayed or recorded on an output unit 7. Reference numeral 8 denotes an instantaneous switch similar to a conventional instantaneous switch.

Figure 2A:
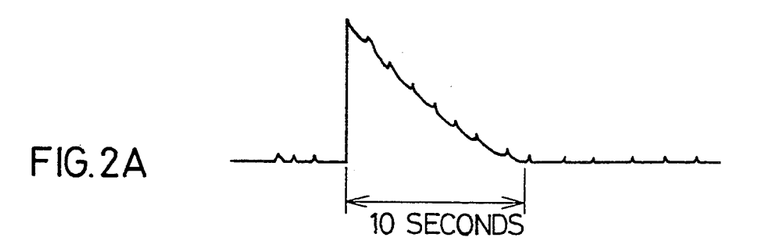
FIGS. 2A-2D are a waveform chart illustrating the operation of the circuit shown in FIG. 1.

Electrocardiographic signals are input in a normal state to the electrocardiographic signal processing circuit through the high-pass filter 2. When a polarization voltage (FIG. 2A) of, for example, approximately +300 mV develops in the preamplifier 1 when the defibrillator 6 is operated, the voltage is amplified by the wide dynamic range of the defibrillator 6 without being saturated. At this time, as a result of the filter switching circuit 4 being operated in synchronization with a trigger signal, the high-pass filter 3 is connected to the circuit for 10 seconds. Electrocardiographic signals (indicated by the solid line in FIG. 2B) in which the low-band components of the superimposed polarization voltage are attenuated greatly are input to the electrocardiographic signal processing circuit 5. During this time, particularly the ST components with many low-band components, of the electrocardiographic signals are slightly distorted as shown in FIG. 2D from the normal state of FIG. 2C. However, the QRS waves are hardly distorted and return to the normal state in 10 seconds.

Figure 2B:
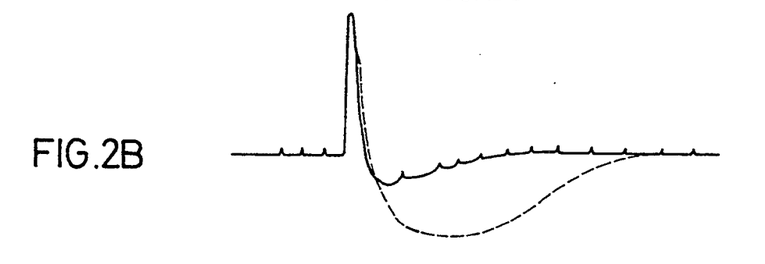
Figure 2C:
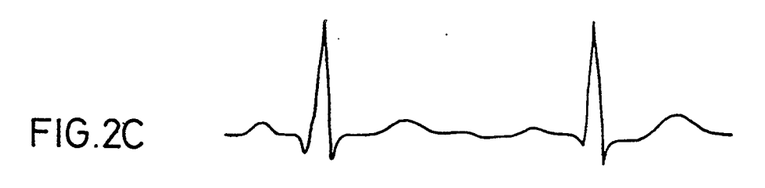
Figure 2D:
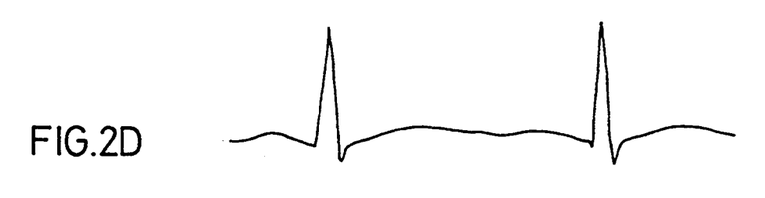

If only the high-pass filter 2 is connected to the circuit 4 for 10 seconds when the polarization voltage (FIG. 2A) develops, an input signal is as indicated by the dotted line in FIG. 2B. The scale-over time in an output unit, for example, in a recorder, becomes quite long. An excessive input signal can be blocked by turning on the instantaneous switch 8 at an electrode switching time or the like.

It is possible in the above-described embodiment to form the high-pass filter 3 in various ways so that the filter 3 has a cut-off frequency higher than that of the high-pass filter 2 even if CR circuits of the same time constant are not used. Instead of forming the second high-pass filter by the high-pass filters 2 and 3, they may be formed independently of each other in such a way that they are connected parallelly so as to be selectable.

Figure 3:
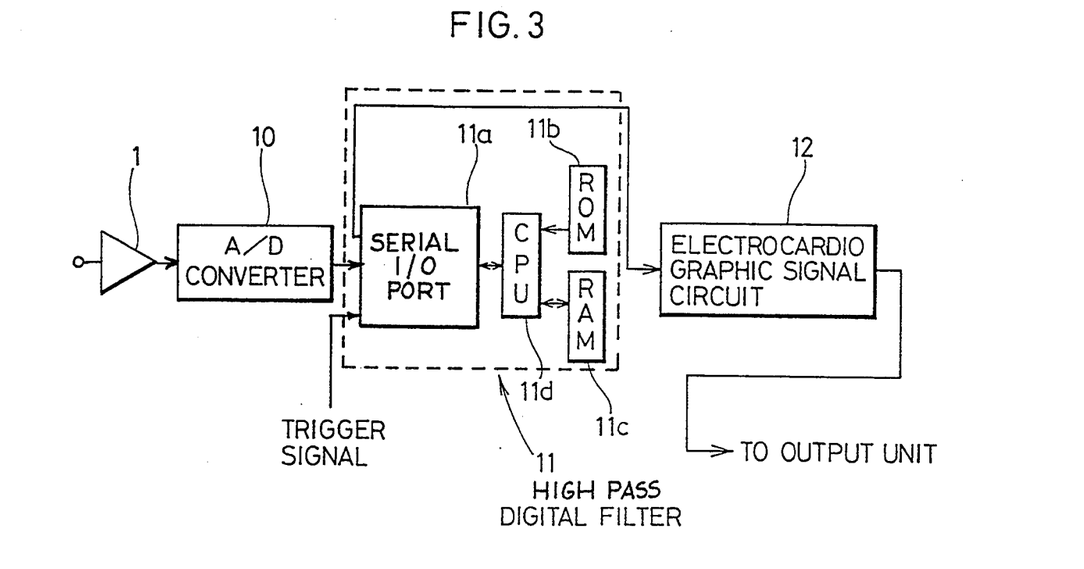
FIG. 3 is a view illustrating the circuitry of the main portion of a defibrillator with an electrocardiographic monitor according to another embodiment of the present invention.

FIG. 3 illustrates the circuitry of a defibrillator with an electrocardiographic monitor according to another embodiment of the present invention. An amplified output from the preamplifier 1 is converted into a digital form by an A/D converter 10 having a dynamic range of 20 bits, i.e., ±5.24 V at, for example, 10 μmV/LSB, and then supplied to a high-pass digital filter 11 employing a CPU. High pass digital filter 11 includes a serial I/O port 11a, a CPU 11d, a ROM 11b and a RAM 11c. Output signals from the filter are converted from the digital form into the analog form by an electrocardiographic signal processing circuit 12 or data-processed as they are in the form of digital signals.

Stored in the ROM 11b are a routine of a high-pass digital filtering operation of a cut-off frequency of 0.3 Hz, which routine is to be executed by the CPU 11d, and a program in which input signals stored in the RAM 11c through the serial I/O port 11a are made to circulate the above routine two times and then output. The use of digital filters in this manner suppresses switching noise or transient signal changes at switching time.

A high-pass digital filter may be formed in such a way that two types of separate digital filters may be connected parallelly or serially so as to be selectable.

Figure 4:
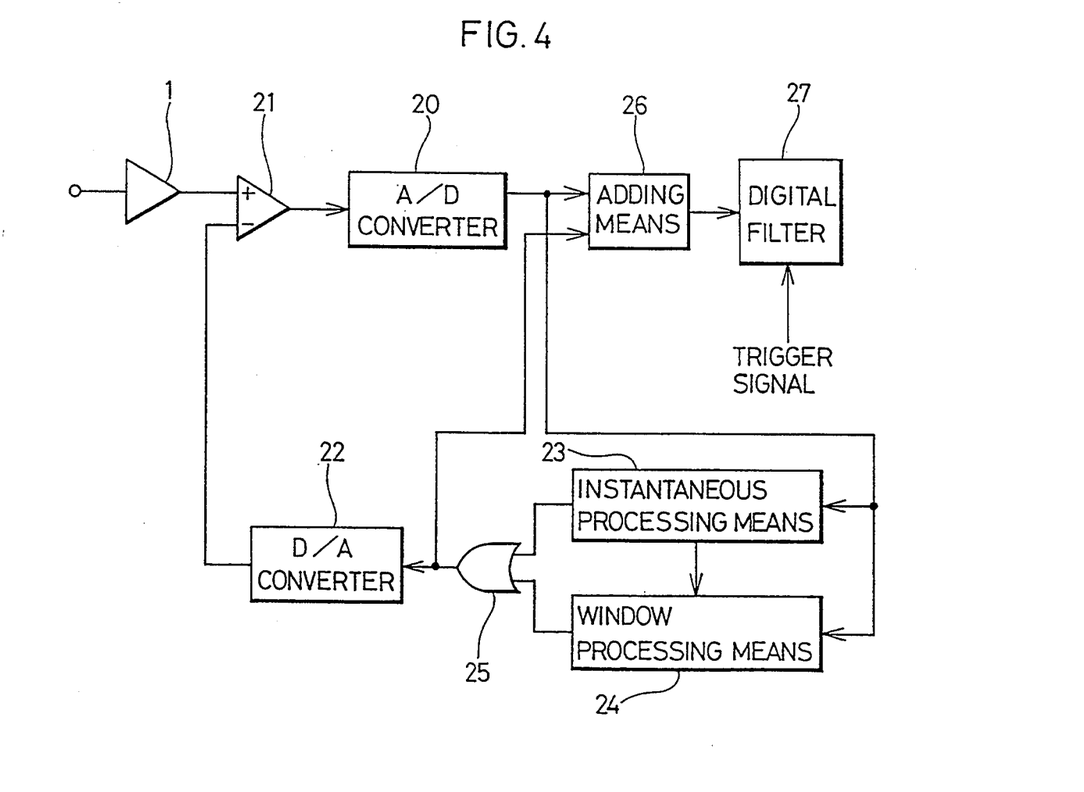
FIG. 4 is a view illustrating the circuitry of the main portion of a defibrillator with an electrocardiographic monitor according to still another embodiment of the present invention.

FIG. 4 illustrates the circuitry of a defibrillator with an electrocardiographic monitor according to still another embodiment of the present invention. In this embodiment, an A/D converter 20 which has a narrow dynamic range of ±5.12 mV at 10 μm V/LSB. 10 bits in terms of input conversion is used in place of the A/D converter 10. Added to the defibrillator are a differential amplifier 21 whose amplified output is supplied to one of the input terminals so that input signals from the A/D converter are always moved to a window W having a width of 1.2 mV (±0.6 mV) within the dynamic range. Instantaneous processing means 23 supply a subtraction signal which decreases in a stepped manner to the other input terminal of the differential amplifier 21 when the defibrillator is operated, in accordance with the output signal level of the A/D converter 20 so that the input signal level outside of the dynamic range of the A/D converter 20 is moved to the window W. Window processing means 24 supplies a subtraction signal having an amplitude corresponding to the window width to the other input terminal through the D/A converter 22 if the input signal is outside of the window W so that the input-signal level of the A/D converter 20 is set within the window W within the dynamic range after the instantaneous processing means is operated. Adding means 26 add a subtraction signal from the instantaneous processing means 23 or the window processing means 24, which subtraction signal is supplied through an OR gate 25, to an output signal from the A/D converter 20 in order to restore the input signal and for supplying the signal to a digital filter 27 having first and second high-pass filtering functions which are selectable.

Figure 5:
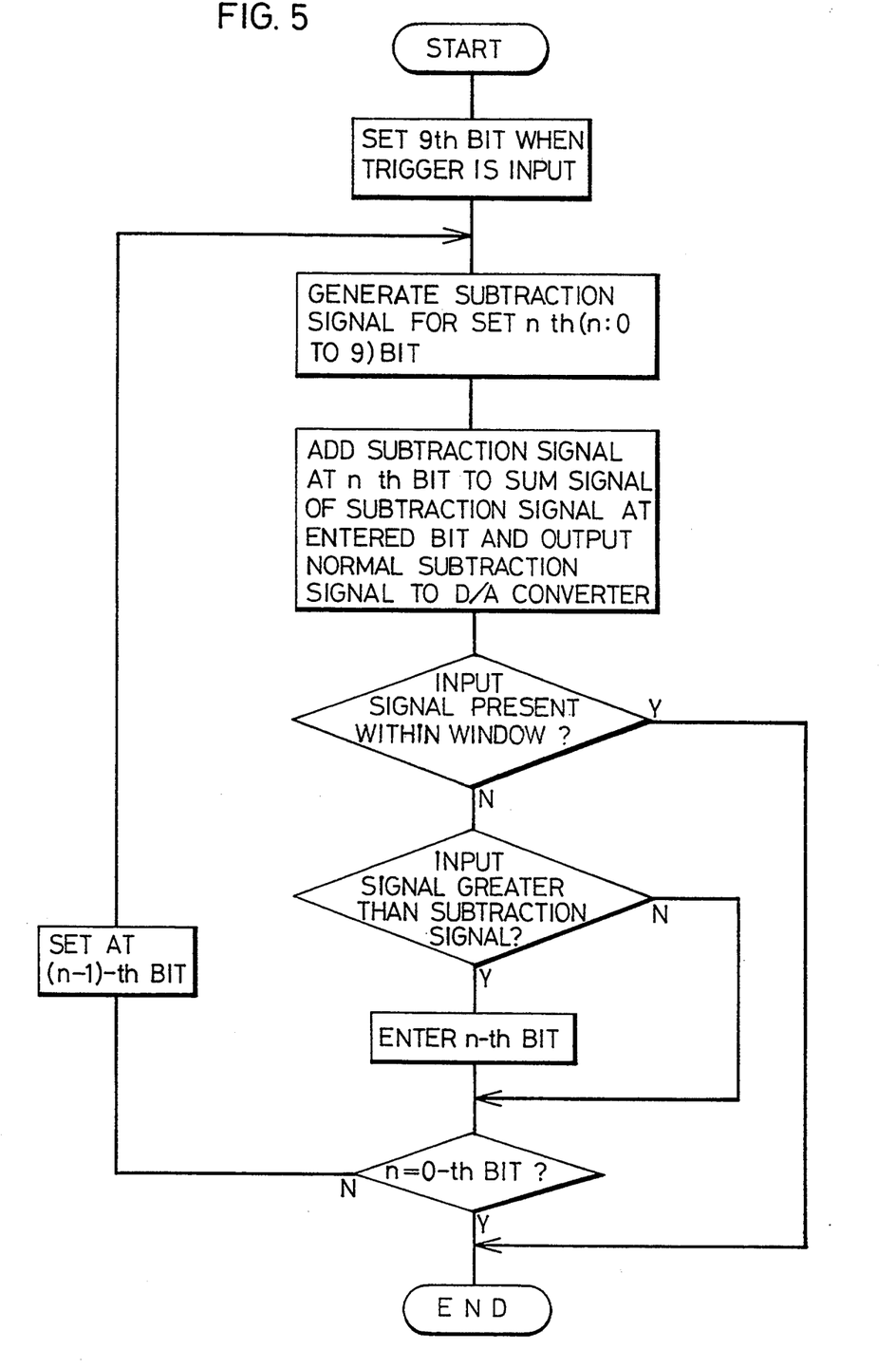
FIG. 5 is a flowchart showing the operation of the circuit according to the embodiment shown in FIG. 4.
Figure 6:
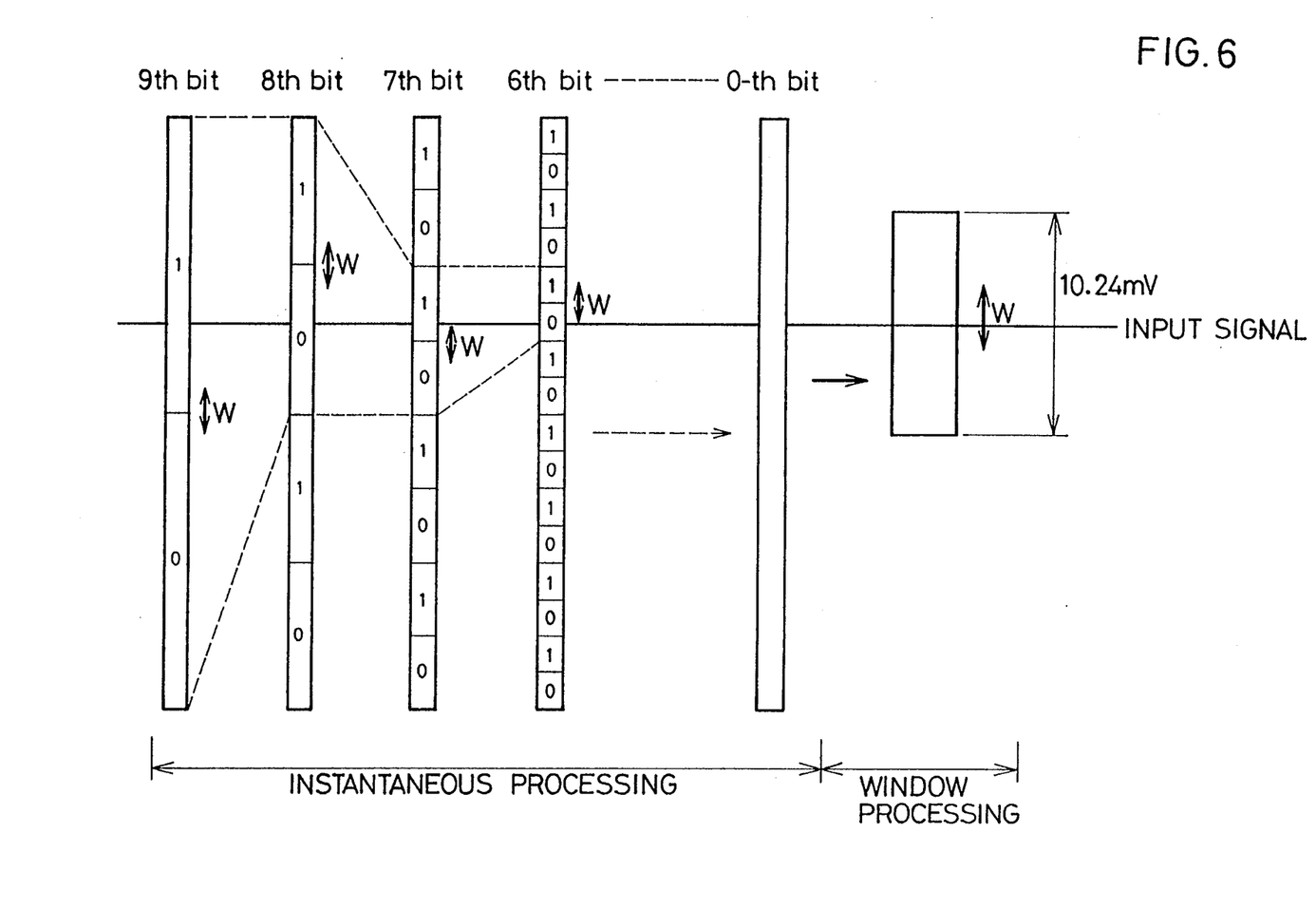
FIG. 6 is a view illustrating the operation of the circuit according to the embodiment shown in FIG. 4.

The various above parts 23 to 27 can be realized by using the common CPU 11d in such a way that a program is added to the above-mentioned ROM 11b. The instantaneous processing means 23 performs the operation shown in the flowchart of FIG. 5. First, the polarity of the output signal from the A/D converter 20 is checked. If it is a +signal, an input conversion operation is performed by the A/D converter 20 as shown in FIG. 6, and a weighting signal (+307.2 mV) at a 9th bit is output as a subtraction signal. Determinations are made whether the input signal is present within the window W and whether the input-signal level is greater or smaller than the window W. If it is greater than the window W as shown in Table 1, the 9th bit is entered, and a weighting signal (153.6 mV) at an 8th bit is added and output. At this time, if the input-signal level is smaller than the added output, it is not entered, and a weighting signal (76.8 mV) at a 7th bit is added and output to the 9th bit. If, however, the input-signal level is greater than the added output, it is entered. The addition signal at the bit entered in this manner is formed to be a subtraction signal. A subtraction/determination operation is performed up to the 0-th bit of +0.6 mV, and the input signal is set within the window W having a width of +0.6 mV. When the input-signal level is set within the window W while the instantaneous processing is being performed, the instantaneous processing is terminated.

TABLE 1

| | 9 | 8 | 7 | 6 | 5 | 4 | 3 | 2 | 1 | 0 |
|---|---|---|---|---|---|---|---|---|---|---|
| D/A | 1 | 0 | 1 | 0 | → | | | | | |

In this way, the instantaneous processing is terminated in a required time of, at most, approximately 20 ms. Thereafter, if the input-signal level is greater than the window W having a width of 1.2 mV set within the dynamic range of 12 mV of the A/D converter 10, a reduction signal of −0.6 mV is added and the result is output. If the input-signal level is smaller than the window W, +0.6 mV is added and output. Thus, the window operation for ensuring that the A/D converter 20 is always operated within the dynamic range is performed.

The operation of this embodiment will now be explained.

Figure 7A:
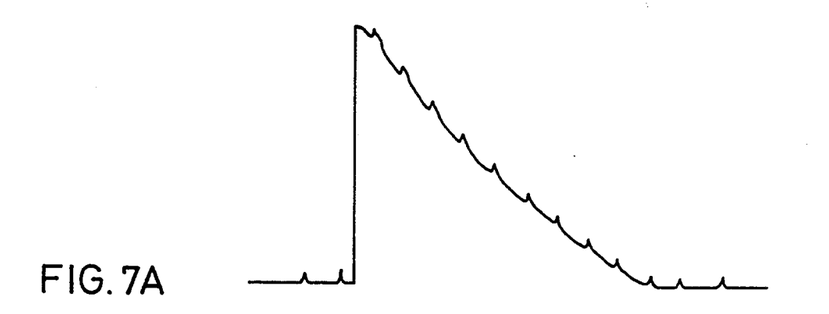
FIGS. 7A-7D are a view illustrating the operating waveforms of the circuit according to the embodiment shown in FIG. 4.
Figure 7B:
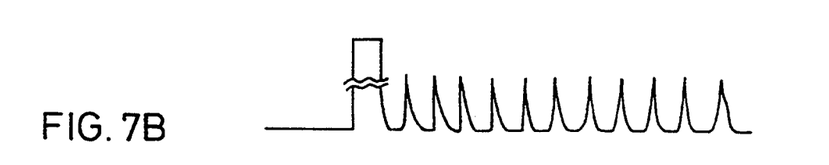
Figure 7C:
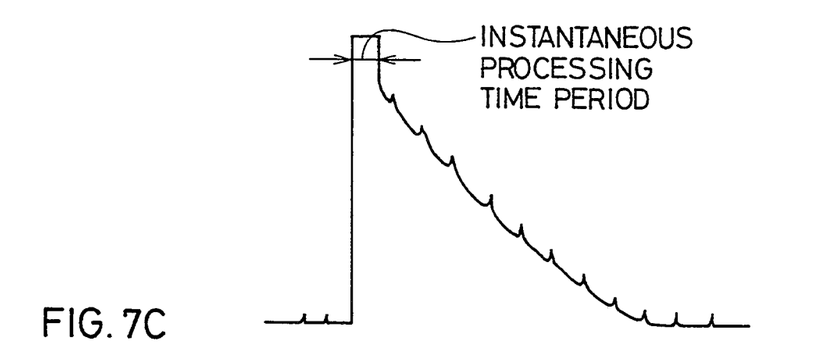

If, for example, a +polarization voltage (FIG. 7A) is input to the preamplifier 1 when the defibrillator is operated, an output signal (FIG. 7B) saturated beyond the dynamic range is output from the A/D converter 20. At this time, the instantaneous processing is performed in synchronization with the receiving of the trigger signal so that the input signal is instantaneously set in the window W. Thereafter, if the input-signal level is outside of the window W, a window processing for performing a subtraction is performed. The input signal is always converted from the analog form into the digital form within a dynamic range of ±5.12 mV of the A/D converter 20. Output signals (FIG. 7B) from the A/D converter 20 change in steps of 0.6 mV as a result of the subtraction signal being decreased in units of +0.6 mV in a window processing step for such input signals whose amplitudes decrease gradually in the form of triangular waves. Therefore, the input signal (FIG. 7A) is restored except in the instantaneous processing region (the time width is enlarged in FIG. 7C) by the signal (FIG. 7C) produced by adding the output signal to the subtraction signal and supplied to the digital filter 27.

Figure 7D:
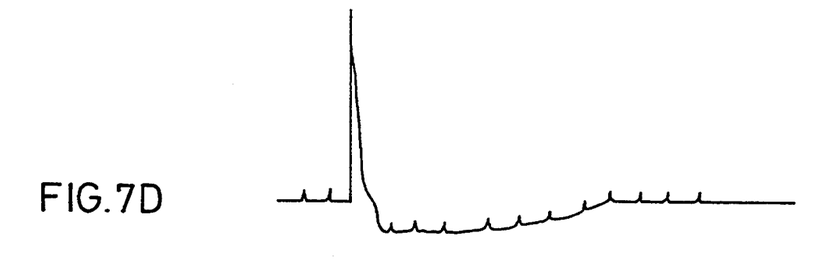

As a result, a conversion operation by a 20-bit A/D converter is equivalently performed by using a 10-bit A/D converter. In the normal state in which the polarization voltage is vanished, if the electrocardiographic signal level is outside of the window W, a follow-up operation in 0.6 mV steps is performed. As a result of the subtraction signal being added, normal electrocardiographic signals with the base line as a reference are subjected to a filtering operation of a time constant of 0.52 seconds and output. The electrocardiographic signal shown in FIG. 7D can be obtained by a filtering operation in which the cut-off frequency is switched from 0.3 Hz to approximately 0.6 Hz for 10 seconds including the instantaneous region.

In the above-described embodiment, the resolution of the A/D converter 20 can be increased in accordance with the amplification of the differential amplifier 21 by interposing an amplifier between the A/D converter 20 and the differential amplifier 21.

Many different embodiments of the present invention may be constructed without departing from the spirit and scope of the present invention. It should be understood that the present invention is not limited to the specific embodiments described in this specification. To the contrary, the present invention is intended to cover various modifications and equivalent arrangements included with the spirit and scope of the claims. The following claims are to be accorded the broadest interpretation, so as to encompass all such modifications and equivalent structures and functions.

What is claimed is:

1. In combination, defibrillator for generating a polarization voltage signal and an electrocardiographic monitor, said monitor comprising:
   a first preamplifier for amplifying electrocardiographic signals received at the first preamplifier, the first preamplifier having a dynamic range corresponding to the amplitude of the polarization voltage signal that is generated by the defibrillator;
   a first high-pass filter to which the electrocardiographic signals amplified by the preamplifier are supplied, the first high pass filter having a predetermined cut-off frequency;
   a second high-pass filter to which the electrocardiographic signals amplified by the first preamplifier are supplied, the second high-pass filter having a cut-off frequency that is higher than the cut-off frequency of the first high-pass filter so that any portion of the polarization voltage signal present within the electrocardiographic signal is attenuated without erasing the electrocardiographic signals;
   filter switching means for actuating the second high-pass filter for a time period corresponding to the time period in which the polarization voltage signal is generated by the defibrillator;
   an electrocardiographic signal processing circuit for processing electrocardiographic signals transmitted through one of the first high pass filter and the first and second high-pass filters; and
   output means for monitoring the electrocardiographic signals processed by the electrocardiographic signal processing circuit.

2. A combination according to claim 1, wherein the second high-pass filter is a high-pass filter having a third-order cut-off frequency of approximately 0.6 Hz, the second high-pass filter further including at least two RC circuits and a second preamplifier, the at least two RC circuits being cascade-connected in two steps through the second preamplifier to the first high-pass filter.

3. A combination according to claim 1, wherein the first and the second high-pass filters include at least one digital filter, the at least one digital filter including an A/D converter for converting an amplified output signal from the first preamplifier into a digital form, and the A/D converter is positioned at an anterior position relative to the digital filter.

4. A combination according to claim 3, wherein the digital filter includes an A/D converter and a differential amplifier, the A/D converter having a dynamic range that is smaller than a dynamic range of the first preamplifier and the differential amplifier including a first and a second input terminal, the first input terminal of the differential amplifier being electrically connected to the first preamplifier, and wherein the differential amplifier is positioned at an anterior position relative to the A/D converter, further comprising:
   instantaneous processing means, the instantaneous processing means for supplying a first subtraction signal corresponding to an output-signal level of the A/D converter to the second input terminal of the differential amplifier through a D/A converter during a time period in which the polarization voltage signal is present to change the input signal level of the A/D converter to within the dynamic range of the first preamplifier;
   window processing means, the window processing means for supplying a second subtraction signal of an amplitude corresponding to a window width of the D/A converter if the window processing means determines that the input-signal level is outside of the window, wherein the second subtraction signal is added to move the input-signal level of the A/D converter to within the dynamic range of the first preamplifier after the instantaneous processing means has supplied the first subtraction signal;
   OR gate means, the OR gate means for inputting at least one of the first and second subtraction signals from the window processing means and the instantaneous processing means, respectively, and generating a subtraction output signal; and
   adding means, the adding means for adding the subtraction output signal from the OR gate means to an output signal from the A/D converter to generate an addition signal and outputting the addition signal to the at least one digital filter.

* * * * *

UNITED STATES PATENT AND TRADEMARK OFFICE
CERTIFICATE OF CORRECTION

PATENT NO. : 5,376,104
DATED : December 27, 1994
INVENTOR(S) : Sakai, et al.

It is certified that error appears in the above-indentified patent and that said Letters Patent is hereby corrected as shown below:

Column 1, Line 15, the phrase "with an electrocardiogram", should read --with an electrocardiographic--

Column 3, Line 22, the phrase "even if CR circuits", should read --even if RC circuits--

Column 4, Line 41, the phrase "width of +0.6 mV", should read --width of ±0.6 mV--

Signed and Sealed this

Eleventh Day of April, 1995

Attest:

BRUCE LEHMAN

Attesting Officer  Commissioner of Patents and Trademarks